US009125575B1

(12) United States Patent
Hekmatshoartabari et al.

(10) Patent No.: US 9,125,575 B1
(45) Date of Patent: Sep. 8, 2015

(54) FLEXIBLE ACTIVE MATRIX CIRCUITS FOR INTERFACING WITH BIOLOGICAL TISSUE

(71) Applicant: International Business Machines Corporation, Armonk, NY (US)

(72) Inventors: Bahman Hekmatshoartabari, White Plains, NY (US); Ali Khakifirooz, Mountain View, CA (US); Ghavam G. Shahidi, Pound Ridge, NY (US); Davood Shahrjerdi, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/185,149

(22) Filed: Feb. 20, 2014

(51) Int. Cl.
*H01L 29/06* (2006.01)
*A61B 5/04* (2006.01)
*H01L 21/84* (2006.01)
*H01L 27/12* (2006.01)
*H01L 27/092* (2006.01)
*H01L 21/8238* (2006.01)

(52) U.S. Cl.
CPC .... *A61B 5/04001* (2013.01); *H01L 21/823871* (2013.01); *H01L 21/823878* (2013.01); *H01L 21/84* (2013.01); *H01L 27/092* (2013.01); *H01L 27/1203* (2013.01)

(58) Field of Classification Search
CPC A61B 5/04001; H01L 21/84; H01L 27/1203; H01L 27/092; H01L 21/823871; H01L 21/823878
See application file for complete search history.

(56) References Cited

U.S. PATENT DOCUMENTS

| 6,946,851 | B2 | 9/2005 | Lee |
| 7,905,013 | B2 | 3/2011 | Zhang |
| 8,247,261 | B2 | 8/2012 | Bedell |
| 8,406,889 | B2 | 3/2013 | Llinas |
| 8,447,392 | B2 | 5/2013 | Llinas |
| 8,452,369 | B2 | 5/2013 | Huys |
| 2009/0299213 | A1 | 12/2009 | Patolsky |
| 2012/0157804 | A1 | 6/2012 | Rogers |
| 2013/0284612 | A1 | 10/2013 | Park |

OTHER PUBLICATIONS

Jose K. Abrham et al., Nanowire Integrated Microelectrode Arrays for Neuroelectronic Applications, 2007 IEEE Region 5 Technical Conference, Apr. 20-21, 2007, pp. 185-188.
Brian p. Timko et al., Design and Implementation of Functional Nanoelectronic Interfaces With Biomolecules, Cells, and Tissue Using Nanowire Device Arrays, IEEE Trans. on Nanotech, v9n3, May 2010, p. 269-280.

*Primary Examiner* — Long Pham
(74) *Attorney, Agent, or Firm* — Louis J. Percello; Otterstedt, Ellenbogen & Kammer, LLP

(57) ABSTRACT

High resolution active matrix nanowire circuits enable a flexible and stretchable platform for probing neural circuits. Fabrication of such circuits includes forming an array of transistors using a semiconductor-on-insulator substrate. Electrically isolated arrays of vertically extending, electrically conductive wires are formed from a doped, electrically conductive layer within the substrate, each of the arrays of wires being electrically connected to a transistor in the array of transistors.

11 Claims, 6 Drawing Sheets

FLEXIBLE ACTIVE MATRIX CIRCUITS FOR INTERFACING WITH BIOLOGICAL TISSUE

FIELD

The present disclosure relates to the physical sciences and, more particularly, to active matrix circuits for interfacing with biological tissue and their fabrication.

BACKGROUND

Electronically interfacing with biological tissue is an effective technique for obtaining biophysical information and/or applying current to such tissue. Signals obtained from tissue including neurons can be employed for purposes such as monitoring or analysis of tissue, neural stimulation, and other purposes.

Nanowires have been incorporated within microelectrode arrays that include silicon substrates. The nanowires can be grown within open pores by electrochemical deposition or by patterning and etching of silicon substrates. The nanowires function as electrodes that can be used to apply electrical signals to biological tissue or to receive signals from such tissue.

BRIEF SUMMARY

In accordance with the principles discussed herein, fabrication methods are disclosed for fabricating active matrix structures An exemplary method is provided that includes obtaining a semiconductor-on-insulator substrate, the substrate including a semiconductor layer, a handle, an electrically insulating layer between the semiconductor layer and the handle, and a doped, electrically conductive layer between the handle and the electrically insulating layer. A plurality of electrically isolated active regions is formed within the semiconductor layer. An array of transistors is formed in the active regions using the semiconductor layer of the substrate. The method further includes forming electrical conductors electrically connecting the transistors to the doped, electrically conductive layer, removing the handle, thereby exposing one or more portions of the doped, electrically conductive layer, and forming a plurality of electrically isolated arrays of vertically extending, electrically conductive wires from the doped, electrically conductive layer, each of the wires being electrically connected to a transistor in the array of transistors.

A further method includes obtaining a CMOS sensor device including a semiconductor layer including an array of electrically isolated active regions, an array of transistors, the transistors being within the active regions of the semiconductor layer, an electrically insulating layer adjoining a bottom surface of the semiconductor layer, a dielectric layer adjoining a top surface of the semiconductor layer, and a doped layer adjoining the electrically insulating layer. The doped layer includes a plurality of electrically isolated arrays of doped, electrically conductive wires, each of the wires extending vertically with respect to the semiconductor layer and being electrically connected to a transistor in the array of transistors. The method further includes causing the wires to contact biological tissue and detecting electrical signals generated by the biological tissue or receiving electrical signals from the biological tissue using the device.

A sensor device is disclosed that includes a semiconductor layer including an array of electrically isolated active regions, an array of transistors, the transistors being within the active regions of the semiconductor layer, an electrically insulating layer adjoining a bottom surface of the semiconductor layer, a dielectric layer adjoining a top surface of the semiconductor layer, a handle layer adjoining the dielectric layer, and a doped layer adjoining the electrically insulating layer, the doped layer including a plurality of electrically isolated arrays of doped, electrically conductive wires. Each of the wires extends vertically with respect to the semiconductor layer and is electrically connected to a transistor in the array of transistors.

As used herein, "facilitating" an action includes performing the action, making the action easier, helping to carry the action out, or causing the action to be performed. Thus, by way of example and not limitation, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

Substantial beneficial technical effects are provided by the exemplary structures and methods disclosed herein. For example, one or more embodiments may provide one or more of the following advantages:

Flexible and stretchable platform for probing neural circuits;
High resolution;
Dense nanowire arrays to allow more accurate readout of small signals by reducing the input impendence;
External wiring optional.

These and other features and advantages of the disclosed methods and structures will become apparent from the following detailed description of illustrative embodiments thereof, which is to be read in connection with the accompanying drawings.

DETAILED DESCRIPTION

A method is disclosed for forming an integrated CMOS sensor having wires for interfacing with neurons. A backplane refers to an array of transistors (active devices). The array of transistors can be used for electrically interfacing with biological neurons. The backplane may also contain address lines, program lines, power supply lines, and storage capacitors which are fabricated using the same process technology as that of the transistors. Passive devices addressed/programmed by the backplane are typically referred to as the frontplane. An active matrix refers to the combination of a backplane and a frontplane.

Active matrix structures such as backplanes are fabricated using techniques described in detail below. Active semiconductor devices are formed using a semiconductor-on-insulator (SOI) substrate. The substrate is thinned using a layer transfer technique or chemical/mechanical processing. Transistors are formed using the semiconductor layer of the substrate, possibly along with additional circuits that provide other functions such as logic, transceiving and/or energy harvesting.

Figure 1:
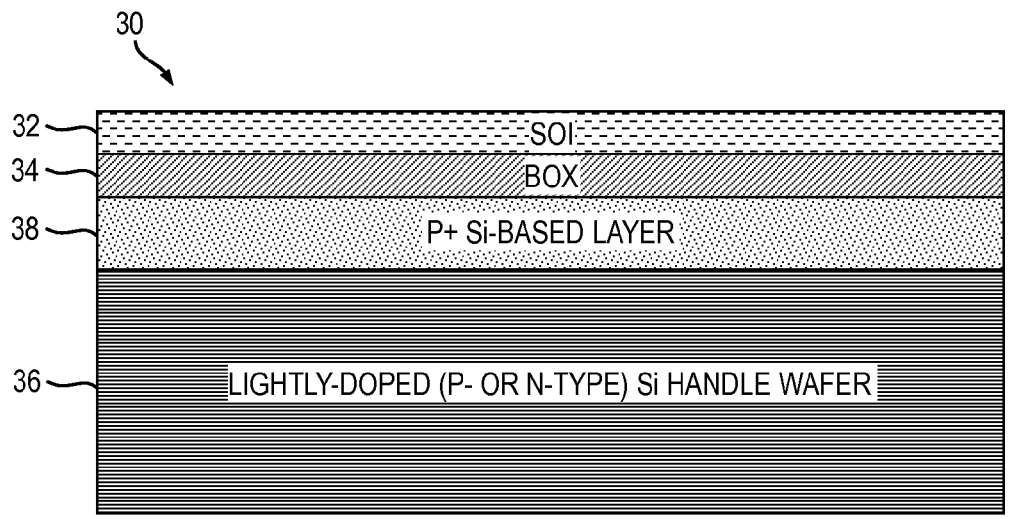
FIG. 1 shows a schematic illustration of a semiconductor on insulator (SOI) substrate.
Figure 2:
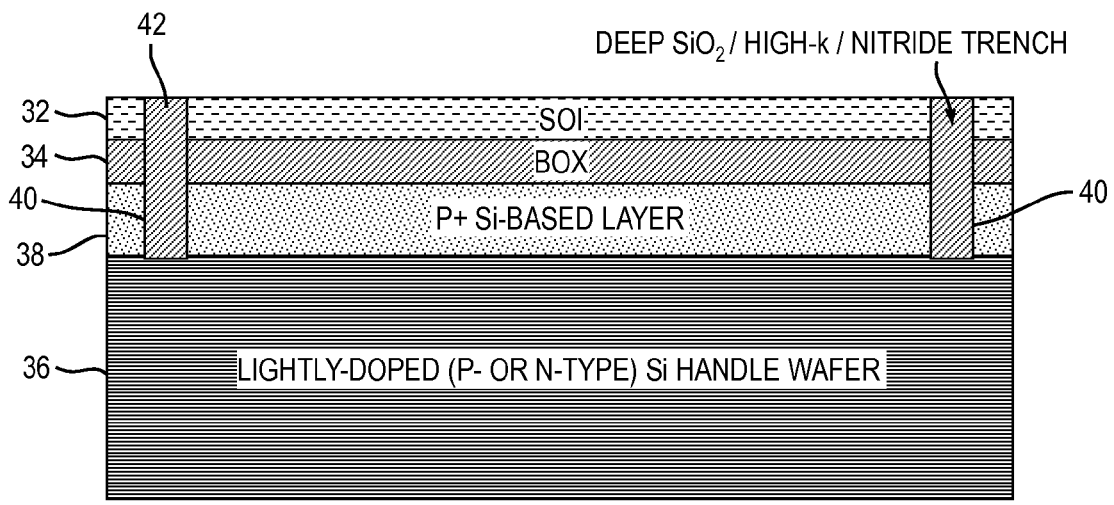
FIG. 2 shows the semiconductor on insulator substrate including deep trenches filled with electrically insulating material.

An exemplary method for fabricating a backplane structure is schematically illustrated in FIGS. 1-4. The starting substrate in this example is a silicon-on-insulator (SOI) wafer 30 comprised of a thin crystalline semiconductor layer (SOI layer) 32 on a buried oxide (BOX) insulator 34, which is in turn on a bulk silicon (handle) substrate 36 (FIG. 2). The thickness of the semiconductor layer 32 is between 2 nm-1 µm in exemplary embodiments, but thicker or thinner layers may be usable in some applications. Relatively thin semiconductor layers facilitate the production of mechanically flexible active matrix structures as discussed further below. Exemplary single crystal materials for the crystalline semiconductor layer 32 include silicon and silicon-containing films such as silicon germanium. The insulator layer 34 in an exemplary embodiment is between 5-200 nm, but may also be thicker or thinner for some applications. Other semiconductor-on-insulator substrates may alternatively be employed, such as silicon-germanium-on-insulator (SGOI), germanium-on-insulator (GOI) and various III-V materials on insulating substrates. The semiconductor-on-insulator substrates may be produced using techniques known in the art. The buried insulator layer 34 in one exemplary embodiment is a high quality silicon dioxide layer that is thermally grown, though other buried insulators such as boron nitride (BN) and aluminum oxide ($Al_2O_3$) may alternatively be employed in some embodiments. High quality buried oxides (BOX) are generally characterized by relatively low interface trap densities ($D_{it}$). The size and shape of the wafer can be chosen by the manufacturer.

The SOI substrate 30 is processed using known device fabrication processes to form a heavily doped layer 38 in the handle substrate 36 that adjoins the electrically insulating layer 34. (See FIG. 1.) In one or more exemplary embodiments, boron doping (for example, greater than 1e 18 $cm^{-3}$) may be provided to form a p+ layer 38. In alternative embodiments, phosphorus doping could be employed form an n+ layer. The heavily doped layer can be formed as a continuous layer as shown, or alternatively in selected areas of the handle substrate beneath the electrically insulating layer, during fabrication of the SOI wafer 30. Ion implantation, possibly conducted through a mask if the layer is formed only in selected areas, can be employed following SOI substrate wafer fabrication to form the doped layer. The layer 38 is between 500 nm-5 µm in depth in a crystalline silicon handle substrate 36 in one or more embodiments.

Referring to FIG. 2, a plurality of trenches 40 is formed in the SOI substrate wafer 30 down to the lightly doped handle portion of the wafer. Reactive ion etch (RIE) is among the techniques that may be employed for forming such trenches.

The trenches are filled with an electrically insulating material 42 such as silicon dioxide, silicon nitride, or a high-k dielectric material. High-k materials, such as hafnium oxide, are understood as having dielectric constants exceeding that of silicon dioxide. The filled trenches may be employed as alignment marks for subsequent processing in some embodiments. Once the trenches are filled, the top surface of the substrate wafer may be polished. Chemical mechanical polishing (CMP) may be employed to provide a planar top wafer surface.

Figure 3:
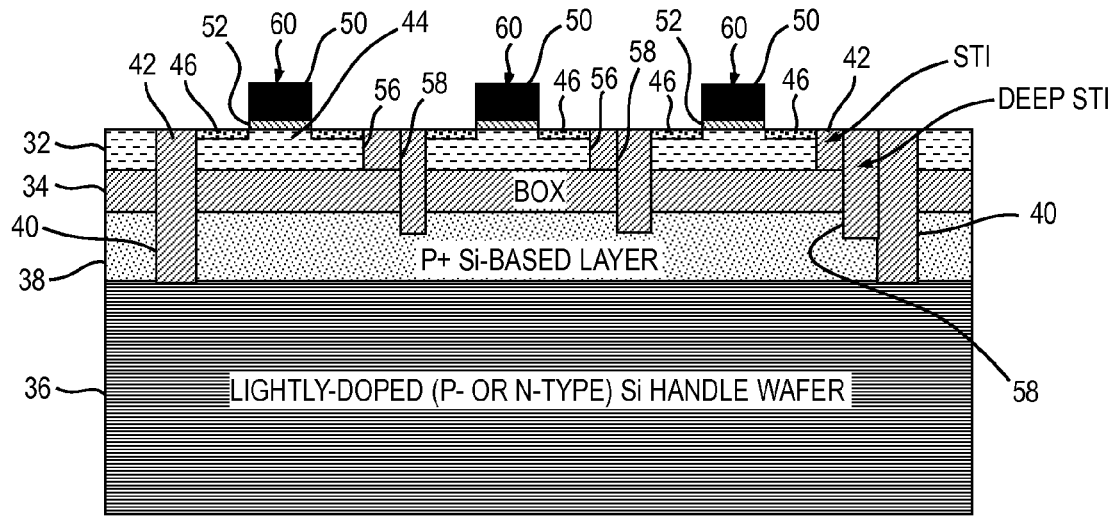
FIG. 3 schematically illustrates transistor fabrication using the semiconductor on insulator substrate shown in FIG. 2.

Referring to FIG. 3, the semiconductor layer 32 is etched to form isolated portions ("islands") that define the active regions of the backplane. Device isolation is typically (though not necessarily) among the first steps performed using conventional processing, prior to transistor fabrication. Conventional techniques for effecting shallow trench isolation (STI) may be employed for providing two adjoining trenches 56, 58. One trench 56 extends through the semiconductor layer 32 to the electrically insulating layer 34. The second trench 58 extends through both the semiconductor layer and electrically insulating layer and into the heavily doped layer 38. Lithography followed by dry etch may be employed to form the trenches. Deposition of electrically insulating materials 42, such as the materials employed for filling the trenches 40 discussed above, follows trench formation. CMP may be employed to planarize the top surface of the wafer.

The backplane elements can be formed using conventional CMOS technology using the SOI wafer 30 to make thin film transistors (TFTs) and other associated elements. The circuit elements can include field-effect or bipolar junction transistors fabricated using standard CMOS processing (implanted or raised source/drain regions, thermal oxide or high-k dielectric, implanted, epitaxial or poly emitters and collectors). ETSOI (extremely thin SOI), PDSOI (partially depleted SOI) and Finfet are among the technologies that can alternatively be employed to form the transistors. ETSOI devices may include raised source/drain regions formed on a crystalline silicon layer having a thickness of less than ten nanometers. The crystalline silicon layer used to form PDSOI devices can be greater than fifty nanometers. In an exemplary structure including n-type transistors, implanted n+ source/drain regions 46 and associated channel regions 44 are formed using the semiconductor layer 32. Ion implantation of the semiconductor layer 32 may be employed for forming source/drain regions while the regions of the semiconductor layer to be used as the channel regions are protected by a mask. A high-k gate dielectric material is deposited and electrically conductive (e.g. metal) gate layers are formed on the layer of gate dielectric material. Schematic illustrations of gate stacks 50 and gate dielectric layers 52 of the depicted FETs 60 are provided. In some embodiments, the gate structures are formed prior to the formation of the source/drain regions. While the transistors are formed in the active regions of the semiconductor layer 32 following shallow trench isolation in the illustrated embodiments, they may alternatively be formed in the active regions prior to isolation.

The source and drain regions in some embodiments can be formed using the semiconductor layer 32 employing conventional, low temperature CMOS technology. For example, highly doped raised source and drain regions (not shown) can be selectively grown epitaxially on the exposed surface of the semiconductor layer 32. Boron doped silicon germanium may be employed to form pFET structures while nFET structures can be formed using phosphorus or arsenic doped silicon germanium. The dopants that provide the conductivity of the source and drain regions can be introduced during the epitaxial growth process. Ion implantation can be employed in place of such in situ doping. Gate electrodes can be deposited by PVD, ALD, CVD or other processes known to those of skill in the art on the gate dielectric layers. The gate electrodes may be comprised of metals such as TiN, TaN, Al, or a combination of such metals. Gate electrode layers may also include a polysilicon layer located on top of a metal material, whereby the top of the polysilicon layer may be silicided.

Figure 4:
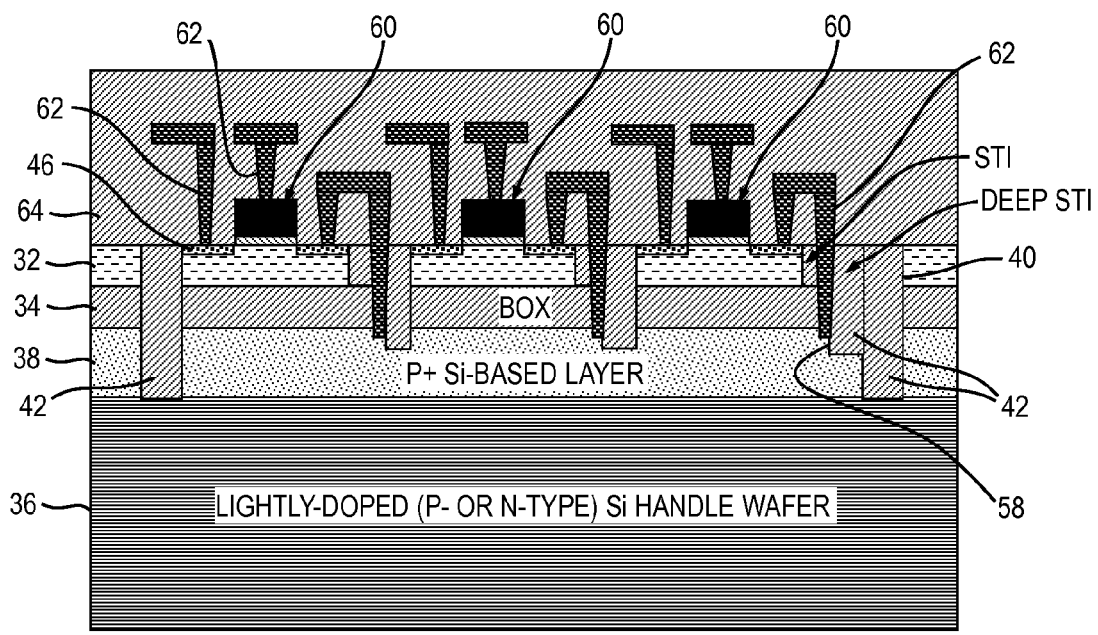
FIG. 4 schematically illustrates back-end-of-line metallization on the semiconductor on insulator substrate shown in FIG. 3.

Electrical communication between the transistors 60 and the heavily doped layer 38 of the handle substrate is provided by deep vias through the electrically insulating layer 34 as shown in FIG. 4. Back end of line (BEOL) metallization processing is conducted to form via conductors 62 and other metal layers within a dielectric layer 64 serving as a passivation and/or planarization layer to form a backplane structure. The dielectric layer 64 chosen should have good adhesion with silicon in embodiments where silicon is employed. It should additionally have a fracture toughness value ($K_{Ic}$) at least comparable to that of silicon in embodiments where silicon is employed to facilitate controlled spalling, as discussed further below. Silicon dioxide, silicon nitride and silicon oxy-nitride have fracture toughness values comparable to that of silicon and are accordingly among the materials that may be chosen for the dielectric layer 64. Using typical insulator growth methods, such as chemical vapor deposition, adhesion between silicon and insulator materials such as silicon dioxide, silicon nitride and silicon oxy-nitride is satisfactory. The via conductors 62 electrically connecting the transistors 60 with highly doped layer 38 are formed in the electrically insulating materials within the trenches 56, 58, the dielectric layer 64, and the electrically insulating layer 34.

Figure 5:
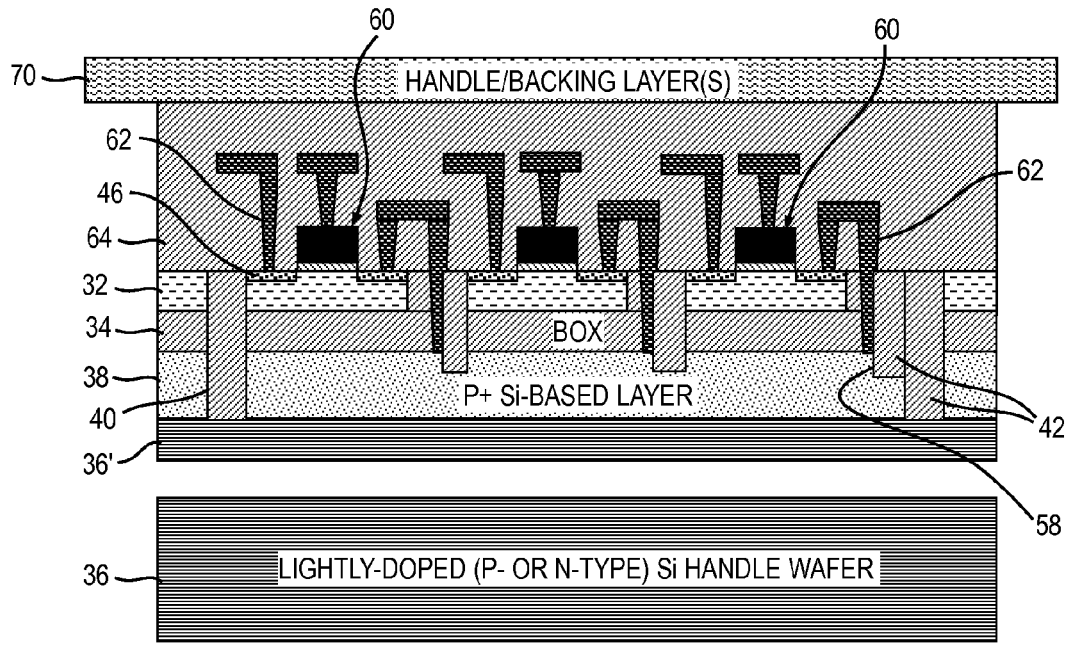
FIG. 5 schematically illustrates thinning the handle portion of the semiconductor on insulator substrate.

Fabrication of the structure shown in FIG. 4 is followed, in some embodiments, by the formation of a handle/backing layer(s) 70. The handle/backing layer(s) in some embodiments includes a stressor metal layer(s) (e.g. nickel) and a flexible handle substrate such as a polyimide layer. An optional insulator layer may be provided to prevent contact of the stressor layer with the electrically conductive elements of the backplane formed during BEOL processing. The flexible handle substrate (e.g. polyimide) is then used for detaching a thin layer of Si by spalling through the handle wafer as shown in FIG. 5. The proper amount of stress to be applied to effect spalling at a desired location in the handle wafer 36 may vary depending on the construction of the backplane structure.

As discussed above, controlled spalling is facilitated by selecting an appropriate insulating layer 64 above the backplane layer. If the electrically insulating layer 64 has a fracture toughness value comparable to silicon, to the first order, the silicon/insulator stack of the exemplary structure can be treated as a single layer in calculating the depth of fracture as a function of stress applied by the stressor layer(s). Therefore, a proper amount of stress can be considered for a desired fracture depth. If the insulating layer 64 has a toughness value larger than that of silicon, the fracture will occur inside the silicon. However, the insulating layer should not have a toughness value materially smaller than that of silicon (or other substrate material, if employed) because the fracture will occur within the insulating layer 64 instead of in the silicon handle wafer 36. The thickness of the metal stressor layer is an additional factor in determining where the fracture will occur in the substrate. Following spalling from the handle wafer 36, a thin residual silicon layer 36' from the substrate 36 that includes the highly doped regions remains beneath the electrically insulating (BOX) layer 34. Stress-induced substrate spalling is disclosed in U.S. Pat. No. 8,247,261, which is incorporated by reference herein.

Figure 6:
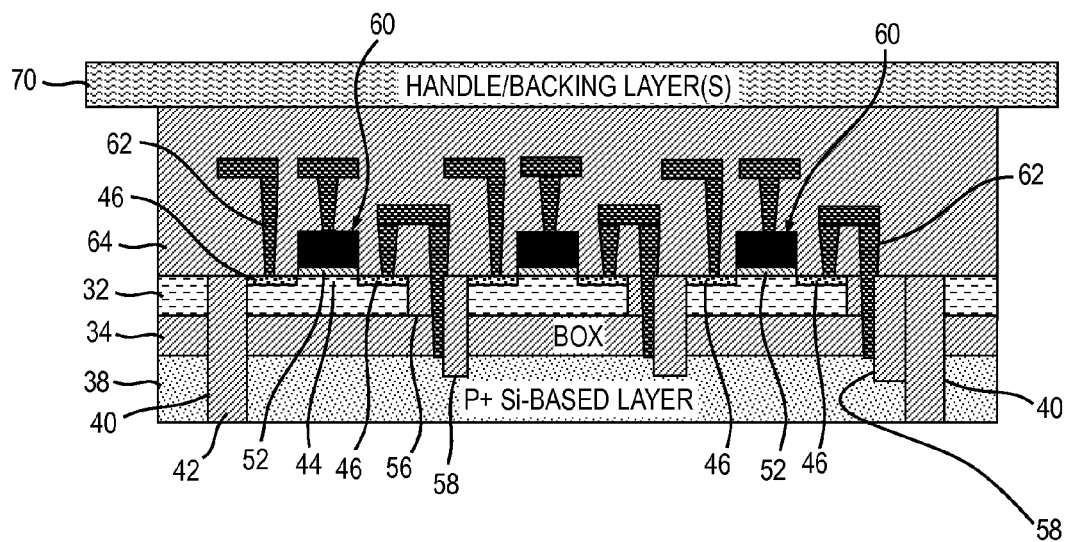
FIG. 6 schematically illustrates selective removal of residual handle portion material.

The thin Si residual layer 36' spalled from the handle wafer 36 is then removed using known techniques, e.g. by selective wet or dry etching to form the structure shown in FIG. 6. The highly doped layer 38 remains following such selective etching. The use of a p-type layer 38 facilitates the etching process in some embodiments as it functions as an etch stop layer. Techniques for removing the residual layer 36' include reactive ion etch and wet etch in TMAH or KOH (tetramethylammonium hydroxide or potassium hydroxide).

It will be appreciated that the handle substrate 36 can be thinned using alternative methods, including chemical/mechanical means such as chemical mechanical planarization, followed by selective etching to remove any residual silicon layer 36'. The handle/backing layer(s) 70 used in such embodiments would not require the same elements required for controlled spalling. A flexible layer of polymeric material could be employed to form the layer 70 in some embodiments. Potassium hydroxide (KOH) and tetramethylammonium hydroxide (TMAH), as discussed above, are among the materials that may be employed for the selective etching of the residual silicon layer to form the exemplary structure of FIG. 6. In embodiments including an n-type, silicon-based layer 38 that does not function as an etch stop, the etching of the residual layer 36' could be discontinued upon the detection of a dopant found in the highly doped layer 38 that is not present in the handle portion of the wafer. Alternatively, a highly doped, n-type silicon based layer could be biased to impede the etching process once the residual silicon layer 36' has been removed.

Figure 7:
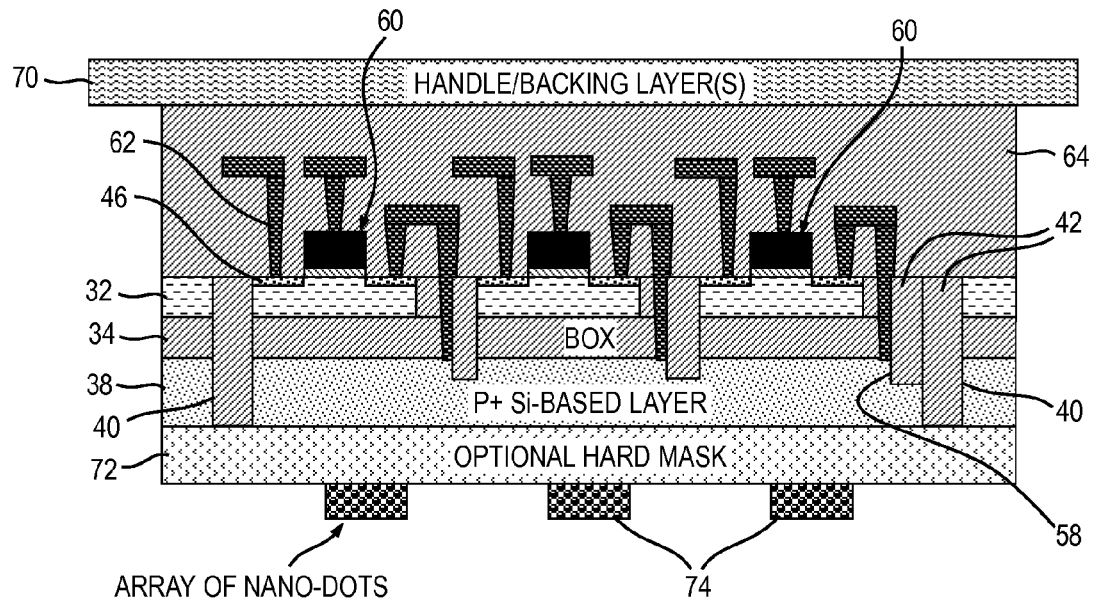
FIG. 7 schematically illustrates the formation of an optional hard mask and a template for patterning.

Referring to FIG. 7, a nitride (e.g. silicon nitride) or oxide (e.g. aluminum oxide) hard mask 72 is optionally formed on the highly doped layer 38. In embodiments wherein the highly doped layer is a p+ silicon-based layer, etch selectivity of the hard mask with respect to p-type silicon is provided. Arrays 74 of dots are formed on the hard mask in embodiments where the hard mask is employed, the dots corresponding in diameter and location to the nanowires to be formed from the highly doped layer 38. In some embodiments, the arrays 74 are formed using a lithography technique such as e-beam, photolithography, and nano-imprint. In other embodiments, self-assembled arrays of particles are formed. The hard mask and arrays 74 of dots formed thereon are employed as a template for subsequent patterning as described below. Gold and silicon dioxide are two exemplary materials from which the dots can be formed. Resist materials that facilitate selective etching are further exemplary materials for forming arrays of dots.

Self-assembly of gold nanoparticles on a metal oxide hard mask (e.g. aluminum oxide, hafnium oxide) can be achieved by procedures known to the art. In one exemplary procedure, the oxide surface is coated with a monolayer of a bifunctional compound having a functionality that adheres to the surface of the oxide (e.g. hydroxamic acid, phosphonic acid) and a charge moeity. For example, pyridine hydroxamic acid methiodide has a hydroxamic acid functionality which self assembles on metal oxide surfaces and a charged moeity (pyridinium salt). After self-assembly of this molecule to form a monolayer on the oxide surface, the positive surface charge of the self-assembled monolayer (SAM) attracts negatively charged molecules or particles. Gold nanoparticles are coated with a ligand. In the case of water soluble gold nanoparticles, the ligand is usually is a charged molecule such as citrate salt which carries a negative charge on the surface of gold nanoparticles. Therefore, when a substrate with positively charged SAM is immersed in a solution of negatively charged gold nanoparticles, the gold particles are attracted to positively charged SAM through coulombic attraction, forming electrostatic bonds and adhering to the surface of the oxide substrate. In one exemplary alternative procedure, molecules having hydroxamic functionality that causes adherence to an oxide surface and thiol functionality that can attract gold nanoparticles from solution (water or solvent) are employed.

As discussed above, a hard mask is not necessarily employed prior to nanowire formation. In some embodiments, a photoresist layer (not shown) is deposited directly on the highly doped layer 38 and patterned to form arrays of photoresist dots corresponding to the arrays of nanowires to be formed by subsequent etching.

Figure 8:
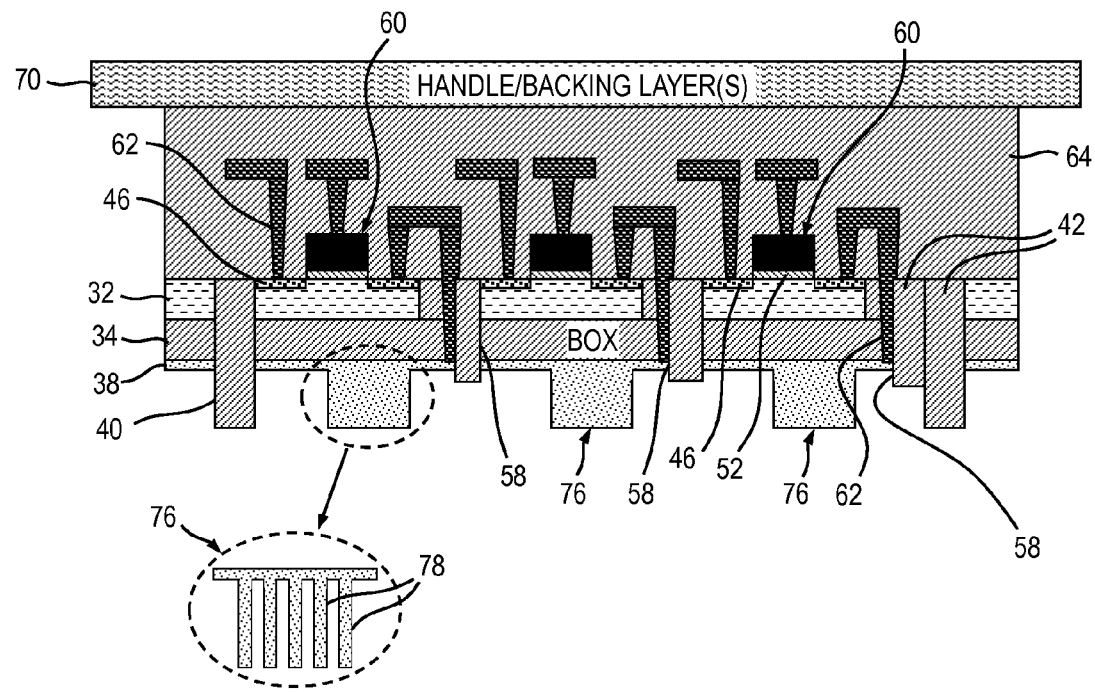
FIG. 8 schematically illustrates patterning and removal of the hard mask to form electrically conductive wires.

Once the structure as shown in FIG. 7 is obtained, the hard mask 72 is patterned. The etch rate of the arrays 74 of dots, being slower than the etch rate of the hard mask 72 on which they are formed, facilitate pattern transfer. The arrays 74 of dots, if not removed during pattern transfer, are subsequently removed once the hard mask 72 has been patterned. Further etching of the patterned hard mask 72 causes the pattern to be transferred from the hard mask to the highly doped layer 38 as shown schematically in FIG. 8, forming arrays 76 of wires corresponding to the arrays 74 of dots. As shown in the insert to FIG. 8, which shows an enlarged portion of a wire array 76, each array 76 includes a plurality of wires 78. The wires 78 extend vertically with respect to the semiconductor layer 32 used to form the transistors 60. The wires, being formed from the electrically conductive, highly doped layer 38, are electrically conductive. The wires of each array are electrically connected to each other by a remaining portion of the highly doped layer 38, from which they extend. Each array 76 of wires 78 is also electrically connected to a transistor 60 by a via conductor 62 formed during earlier processing. The arrays 76 are electrically isolated from each other by the electrically insulating material within the trenches 58. The height of each wire 78 is between 500 nm-5 µm in one or more embodiments. The wires in each array 76 are substantially equal in height. The width of each wire is in the range of 100 nm-10 µm in one or more embodiments. The width is substantially uniform in some embodiments, though it may vary between base and tip in other embodiments. The spacing between wires ranges from 100 nm-10 µm in exemplary embodiments.

Figure 9:
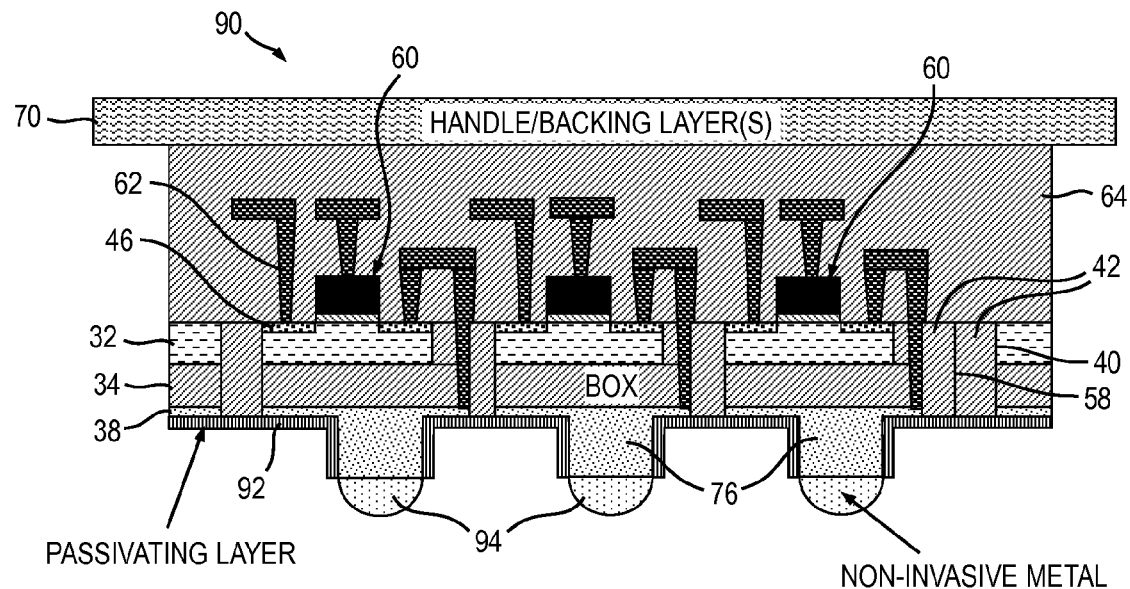
FIG. 9 schematically illustrates passivation of the wires and deposition of a metal on the wire tips.

FIG. 9 shows an exemplary CMOS sensor device 90 for interfacing with neurons. A passivating layer 92 is formed on the highly doped layer 38, including the highly doped wires 78. The passivating layer 92 is formed from an electrically insulating material such as silicon dioxide, aluminum oxide, or a high-k dielectric material. Portions of the passivating layer are removed to expose the wire tips while the sides of the wires and associated highly doped layer remain covered. A patterned polymer layer (not shown) is used in some embodiments to facilitate selective etching of the passivating layer 92 to expose the wire tips while leaving the remaining portions of the passivating layer in place. A layer 94 of a soft, non-invasive metal such as gold is deposited on each of the wire tips. Selective electroplating of the wire tips is employed to form the metal layers 94 in one or more embodiments. An evaporation and liftoff metallization process is employed in other embodiments. The polymer layer is removed following selective etch of the tips and metal deposition.

Figure 10:
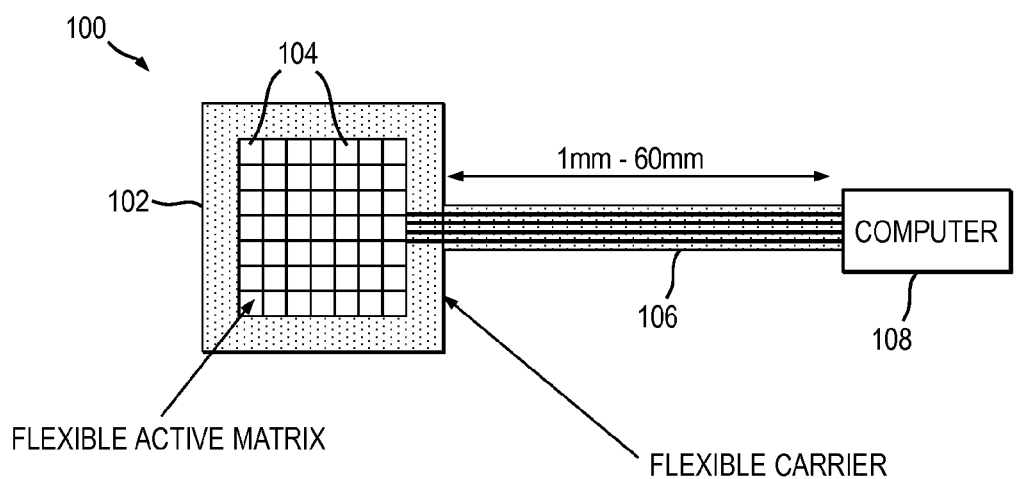
FIG. 10 schematically illustrates assembly of active matrix structures as shown in FIG. 9 on a flexible substrate.

FIG. 10 schematically illustrates a flexible active matrix assembly 100 including a structure as shown in FIG. 9 on a flexible carrier 102. The flexible carrier 102 is a polydimethylsiloxane (PDMS) sheet in one or more embodiments. The carrier 102 is not necessarily stretchable. A flexible active matrix can be mounted to the flexible carrier using an adhesive layer or by bonding. Each square 104 represents an electrically isolated active area of the exemplary structure 90. The exemplary assembly 100 further includes a wire assembly 106 for communicating information relating to the test subject (e.g. neurons) to a computer 108 and/or for sending electrical signals to the test subject via the wires 38.

Figure 11:
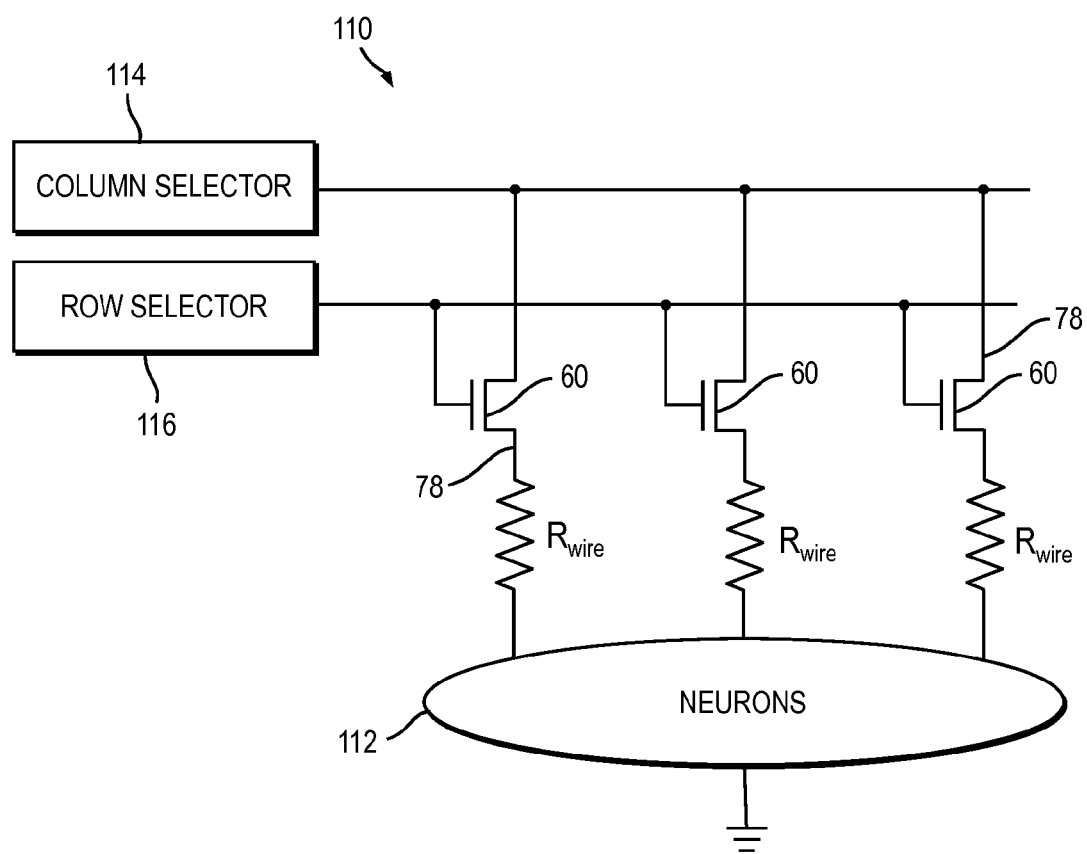
FIG. 11 is a schematic illustration of a circuit using an active matrix structure as shown in FIG. 9.

FIG. 11 schematically illustrates an electrical circuit 110 for neuron monitoring that can be employed in conjunction with devices as described herein. In exemplary embodiments wherein n-type transistors 60 are employed, the wires 78 are electrically connected between the transistor sources and the neurons 112 to be analyzed. The exemplary circuit further includes a column selector 114 and a row selector 116. The column selector is connected to the transistor drain and the row selector is connected to the transistor gate. The sensor device 90, having wires 78 that are integrated with integrated circuits, is capable of receiving signals from and/or applying signals to large numbers of neurons in one or more embodiments. Mechanical flexibility of the device facilitates its application to non-planar surfaces as it can be conformed to surface contours. The wires 78 contact biological tissue surfaces in some embodiments and extend within such tissue in other embodiments.

Given the discussion thus far, an exemplary fabrication method is provided that includes obtaining a semiconductor-on-insulator substrate 30, the substrate including a semiconductor layer 32, a handle 36, an electrically insulating layer 34 between the semiconductor layer and the handle substrate, and a doped, electrically conductive layer 38 between the handle and the electrically insulating layer. A plurality of electrically isolated active regions is formed within the semiconductor layer. An array of transistors is formed in the active regions using the semiconductor layer 32 of the substrate. The method further includes forming electrical conductors 62 electrically connecting the transistors to the doped, electrically conductive layer 38, removing the handle, thereby exposing one or more portions of the doped, electrically conductive layer, and forming a plurality of electrically isolated arrays 76 of vertically extending, electrically conductive wires 78 from the doped, electrically conductive layer 38, each of the wires 78 being electrically connected to a transistor 60 in the array of transistors. In accordance with a further embodiment of the method, each wire includes a body portion and a tip, the method further including the steps of forming a passivating layer 92 on the wires and forming a metal layer 94 on the tips of the wires, the metal layers being electrically coupled to the body portions of the wires. FIG. 9 shows a device 90 obtained following such fabrication steps.

A sensor device provided in accordance with one or more embodiments includes a semiconductor layer 32 including an array of electrically isolated active regions, an array of transistors 60, the transistors being within the active regions of the semiconductor layer, an electrically insulating layer 34 adjoining a bottom surface of the semiconductor layer, a dielectric layer 64 adjoining a top surface of the semiconductor layer, a handle layer 70 adjoining the dielectric layer, and a doped layer 38 adjoining the electrically insulating layer, The doped layer 38 includes a plurality of electrically isolated arrays 76 of doped, electrically conductive wires 78, each of the wires extending vertically with respect to the semiconductor layer 32 and being electrically connected to a transistor 60 in the array of transistors. In one or more embodiments, each of the wires 78 further includes a highly doped body portion, a passivating layer 92 coating the body portion, and a metal tip 94 electrically coupled to the highly doped body portion. The wires 78 have heights ranging between 500 nm-5 µm and widths ranging between 100 nm and 10 µm. Wire arrays 76 electrically connected to each transistor 60 each include at least ten (10) and up to $10^4$ wires 78 in embodiments of the sensor device. Some embodiments of the sensor device further include a column selector 114 and a row selector 116, the transistors 60 being electrically connected to the column and row selectors.

A further method includes obtaining a CMOS sensor device including a semiconductor layer including an array of electrically isolated active regions, an array of transistors, the transistors being within the active regions of the semiconductor layer, an electrically insulating layer adjoining a bottom surface of the semiconductor layer, a dielectric layer adjoining a top surface of the semiconductor layer, a handle layer adjoining the dielectric layer, and a doped layer adjoining the electrically insulating layer. The doped layer includes a plurality of electrically isolated arrays of doped, electrically conductive wires, each of the wires extending vertically with respect to the semiconductor layer and being electrically connected to a transistor in the array of transistors. The method further includes causing the wires to contact biological tissue and detecting electrical signals generated by the biological tissue or receiving electrical signals from the biological tissue using the device. In some embodiments, the biological tissue includes neurons 112.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Terms such as "above", "below", "top" and "bottom" are generally employed to indicate relative positions as opposed to relative elevations unless otherwise indicated. It should also be noted that, in some alternative implementations, the steps of the exemplary methods may occur out of the order noted in the figures. For example, two steps shown in succession may, in fact, be executed substantially concurrently, or certain steps may sometimes be executed in the reverse order, depending upon the functionality involved.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method comprising:
    obtaining a semiconductor-on-insulator substrate, the substrate including a semiconductor layer, a handle, an electrically insulating layer between the semiconductor layer and the handle, and a doped, electrically conductive layer between the handle and the electrically insulating layer;
    forming a plurality of electrically isolated active regions within the semiconductor layer;
    forming an array of transistors in the active regions using the semiconductor layer of the substrate;
    forming electrical conductors electrically connecting the transistors to the doped, electrically conductive layer;
    removing the handle, thereby exposing one or more portions of the doped, electrically conductive layer, and
    forming a plurality of electrically isolated arrays of vertically extending, electrically conductive wires from the doped, electrically conductive layer, each of the wires being electrically connected to a transistor in the array of transistors.

2. The method of claim 1, wherein each wire includes a body portion and a tip, further including the steps of forming a passivating layer on the wires and forming a metal layer on the tips of the wires, the metal layers being electrically coupled to the body portions of the wires.

3. The method of claim 2, further including the steps of attaching a flexible handle layer to the substrate, providing a flexible carrier, and attaching the handle layer to the flexible carrier.

4. The method of claim 2, wherein the step of forming the plurality of arrays of electrically conductive wires further includes:
    forming a plurality of arrays of dots over the doped, electrically conductive layer, the dots having etch selectivity with respect to the doped, electrically conductive layer,
    etching the doped, electrically conductive layer to form the wires beneath the dots, and
    removing the dots.

5. The method of claim 1, wherein the wires have heights ranging between 500 nm-5 μm and widths ranging between 100 nm and 10 μm.

6. The method of claim 5, further including electrically connecting the transistors to column and row selectors.

7. A method comprising:
    obtaining a CMOS sensor device including:
        a semiconductor layer including an array of electrically isolated active regions,
        an array of transistors, the transistors being within the active regions of the semiconductor layer,
        an electrically insulating layer adjoining a bottom surface of the semiconductor layer,
        a dielectric layer adjoining a top surface of the semiconductor layer, and
        a doped layer adjoining the electrically insulating layer and including a plurality of electrically isolated arrays of doped, electrically conductive wires, each of the wires extending vertically with respect to the semiconductor layer and being electrically connected to a transistor in the array of transistors;
    causing the wires to contact biological tissue, and
    detecting electrical signals generated by the biological tissue or receiving electrical signals from the biological tissue using the device.

8. The method of claim 7, wherein the wires have heights ranging between 500 nm-5 μm and widths ranging between 100 nm and 10 μm.

9. The method of claim 8, further including the step of conforming the device to a surface configuration of the tissue.

10. The method of claim 9, wherein each of the wires includes a metal tip, further including causing the metal tips of the wires to contact the tissue.

11. The method of claim 9, wherein the tissue comprises neurons.

* * * * *